United States Patent [19]

Druzgala

[11] Patent Number: 5,849,788
[45] Date of Patent: *Dec. 15, 1998

[54] COMPOUND FOR TREATMENT OF CARDIAC ARPHYTHMIA, SYNTHESIS, AND METHODS OF USE

[75] Inventor: Pascal Druzgala, Gainesville, Fla.

[73] Assignee: ARYX Therapeutics, Los Altos Hills, Calif.

[ * ] Notice: The term of this patent shall not extend beyond the expiration date of Pat. No. 5,364,880.

[21] Appl. No.: 468,602

[22] Filed: Jun. 6, 1995

Related U.S. Application Data

[60] Division of Ser. No. 260,869, Jun. 16, 1994, Pat. No. 5,440,054, which is a continuation-in-part of Ser. No. 078,371, Jun. 16, 1993, Pat. No. 5,364,880.

[51] Int. Cl.$^6$ .................. A61K 31/36; C07D 307/80; C07D 307/81
[52] U.S. Cl. .................. 514/469; 549/467; 549/468
[58] Field of Search .................. 514/469; 549/467, 549/468

[56] References Cited

U.S. PATENT DOCUMENTS

| | | | |
|---|---|---|---|
| 3,248,401 | 4/1966 | Tondeur et al. | 260/346.2 |
| 4,931,464 | 6/1990 | Grover et al. | 514/423 |
| 4,962,095 | 10/1990 | Grover et al. | 514/91 |
| 5,175,187 | 12/1992 | Baligadoo | 514/464 |
| 5,364,880 | 11/1994 | Druzgala | 514/469 |
| 5,440,054 | 8/1995 | Druzgala | 549/467 |

FOREIGN PATENT DOCUMENTS

| | | |
|---|---|---|
| 1299247 | 12/1972 | United Kingdom . |
| 90/07330 | 7/1990 | WIPO . |
| 92/20331 | 11/1992 | WIPO . |

OTHER PUBLICATIONS

Xu, Yungen et al. (1992) "Synthesis of 3–substituted diiodobenzoylindole derivatives" Chemical Abstracts 116(5):756, abstract No. 41241m.

Bigger, J.T. Jr. (1987) "Why patients with congestive heart failure die: arrhythmias and sudden cardiac death" Circulation 75 (suppl IV):28–35.

Smith, W.M. (1985) "Epidemiology of Congestive Heart Failure" The American Journal of Cardiology 55:3A–8A.

The Cardiac Arrhythmia Supprression Trial (CAST) Investigators (1989) "Preliminary Report: Effect of Encainide and Flecainide on Mortality in a Randomized Trial of Arrhythmia Suppression after Myocardial Infarction" The New England Journal of medicine 321(6):406–412.

Goldstein, S. (1991) "Identification of Patients at Risk for Sudden Death in Congestive Heat Failure" J. Clin. Pharmacol. 31:1085–1088.

McKee, P.A. et al. (1971) "The Natural History of Congestive Heart Failure: The Framingham Study" The New England Journal of Medicine 285(26):1441–1446.

Sami, M.H. (1991) "Sudden Death in Congestive Heart Failure" J. Clin. Pharmacol. 31:1081–1084.

*Primary Examiner*—Ba K. Trinh
*Attorney, Agent, or Firm*—Saliwanchik, Lloyd & Saliwanchik

[57] ABSTRACT

Described is a novel compound and method, useful for treatment of cardiac arrhythmias, especially useful in patients with congestive heart failure (CHF). A process for synthesizing the novel compound is also described.

16 Claims, 12 Drawing Sheets

COMPOUND FOR TREATMENT OF CARDIAC ARPHYTHMIA, SYNTHESIS, AND METHODS OF USE

CROSS-REFERENCE TO A RELATED APPLICATION

This is a division of application Ser. No. 08/260,869, filed Jun. 16, 1994, now U.S. Pat. No. 5,440,054, which is a continuation-in-part of application Ser. No. 08/078,371, filed Jun. 16, 1993 now U.S. Pat. No. 5,364,880.

BACKGROUND OF THE INVENTION

Congestive heart failure (CHF) is a disease affecting approximately 2% of the population of the United States (Sami, M. H. [1991] *J. Clin. Pharmacol* 31:1081). Despite advances in the diagnosis and treatment of CHF, the prognosis remains poor with a 5-year mortality rate higher than 50% from the time of diagnosis (McFate Smith, W. [1985] *Am. J. Cardiol.* 55:3A; McKee, P. A., W. P. Castelli, P. M. McNamara, W. B. Kannel [1971] *N. Engl. J. Med.* 285:1441). In patients with CHF, the rate of survival is lowest in those patients with severe depression of left ventricular function and patients who have frequent ventricular arrhythmias. Patients with ventricular arrhythmias and ischemic cardiomyopathy have an increased risk of sudden death. The presence of ventricular tachycardia in patients with severe CHF results in a three-fold increase in sudden death compared to those without tachycardia (Bigger, J. T., Jr. [1987] *Circulation* 75(suppl.IV):28). Because of the high prevalence of sudden unexpected death in patients with CHF, there has been a growing interest in the prognostic significance of arrhythmias in these patients.

Several compounds have been used in the management of cardiac arrhythmias in patients with congestive heart failure. Unfortunately, antiarrhythmic drug therapy has been disappointing. The efficacy of antiarrhythmic drugs markedly decreases as left ventricular function declines, such that only a small fraction of patients with CHF are responsive to antiarrhythmic therapy. No antiarrhythmic drug has prevented sudden death in patients with CHF. There is even a question of increased mortality associated with certain antiarrhythmic drugs (the CAST investigators [1989] *N. Engl. J. Med.* 321:406).

Scientists define tachycardia and ventricular fibrillation as being of multiple nature. It now seems clear, and is accepted in the art, that re-entry is the underlying mechanism to most sustained arrhythmias. Prolonging ventricular repolarization as a means of preventing ventricular arrhythmias has consequently received renewed attention. This points to Class-III agents as drugs of choice in the treatment of arrhythmias. A Class-III agent, as referred to herein, is an agent which is classified as such in the Vaughan-Williams classification of antiarrhythmic drugs. A Class-III agent exerts its primary antiarrhythmic activity by prolonging cardiac action potential duration (APD), and thereby the effective refractory period (ERP), with no effect on conduction. These electrophysiological changes, which are brought about by blockade of cardiac potassium channels, are well known in the art. Because the blockade of cardiac potassium channels is not associated with depression of the contractile function of the heart, Class-III agents are particularly attractive for use in patients with CHF. Unfortunately, the existing Class-Ill agents are limited in their utility by additional pharmacological activities, lack of good oral bioavailability, or a poor toxicity profile. The only two Class Ill agents currently marketed are bretylium (iv. only) and amiodarone (i.v. and p.o.).

Amiodarone is an antiarrhythmic agent having vasodilator properties that may benefit patients with severe heart failure. Amiodarone has been shown to improve survival of post-myocardial infarction patients with asymptomatic high-grade ventricular arrhythmias, and it proved efficacious in patients resistant to other antiarrhythmic drugs without impairing left ventricular function. Cardioprotective agents and methods which employ amiodarone in synergistic combination with vasodilators and beta blockers have been described for use in patients with coronary insufficiency (U.S. Pat. No. 5,175,187). Amiodarone has also been described for reducing arrhythmias associated with CHF as used in combination with antihypertensive agents, e.g., (S)-1-[6-amino-2-[[hydroxy(4-phenylbutyl)phosphinyl] oxyl]-L-proline (U.S. Pat. No. 4,962,095) and zofenopril (U.S. Pat. No. 4,931,464). However, amiodarone is a difficult drug to manage because of its numerous side effects, some of which are serious.

The most serious long-term toxicity of amiodarone derives from its kinetics of distribution and elimination. It is absorbed slowly, with a low bioavailability and relatively long half-life. These characteristics have clinically important consequences, including the necessity of giving loading doses, a delay in the achievement of full antiarrhythmic effects, and a protracted period of elimination of the drug after its administration has been discontinued.

Amiodarone also can interact negatively with numerous drugs including aprindine, digoxin, flecainide, phenytoin, procainamide, quinidine, and warfarin. It also has pharmacodynamic interactions with catecholamines, diltiazem, propranolol, and quinidine, resulting in alpha- and beta-antagonism, sinus arrest and hypotension, bradycardia and sinus arrest, and torsades de pointes and ventricular tachycardias, respectively. There is also evidence that amiodarone depresses vitamin K-dependent clotting factors, thereby enhancing the anticoagulant effect of warfarin.

Numerous adverse effects limit the clinical applicability of amiodarone. Important side effects can occur including corneal microdeposits, hyperthyroidism, hypothyroidism, hepatic dysfunction, pulmonary alveolitis, photosensitivity, dermatitis, bluish discoloration, and peripheral neuropathy.

There is no Class-III agent presently marketed that can be used safely in patients with CHF. The cardiovascular drug market is the largest in any field of drug research, and an effective and safe Class-III antiarrhythmic agent useful in patients with CHF is expected to be of substantial benefit. Therefore, a drug which could successfully improve the prognosis of CHF patients, but with a safety profile much improved over that of amiodarone, would be extremely useful and desired.

BRIEF SUMMARY OF THE INVENTION

The subject invention pertains to novel compounds, and compositions comprising the compounds, for the treatment of cardiac arrhythmias. The subject invention further concerns a method of making the novel compounds. The novel compounds are rapidly metabolized analogs of amiodarone, having the distinct and advantageous characteristic of being metabolized to a less lipophilic compound. This results in an improved safety profile. The new compounds can have particular utility for treating life-threatening ventricular tachyarrhythmias, especially in patients with congestive heart failure (CHF). The product can also provide effective management for ventricular arrhythmias and supraventricular arrhythmias, including atrial fibrillation and re-entrant tachyarrhythmias involving accessory pathways.

More specifically, the novel compounds have the particular advantage of reducing the numerous side effects observed with the drugs currently available for treatment of these cardiac arrhythmias. For example, the compound of choice currently used for treating cardiac arrhythmias is amiodarone, which has side effects that can be serious.

Also disclosed are novel synthesis procedures for the production of the novel compounds. One of the novel synthesis procedures essentially involves acylation of salicylaldehyde followed by cyclization and chain elongation reactions to form methyl-2-benzofuraneacetate. This compound is reacted with p-anisoylchloride involving a Friedel-Crafts type reaction which can use $SnCl_4$ as a catalyst. The compound resulting from the Friedel-Crafts reaction is then converted from the acetate to its carboxylic acid form. The methoxybenzoyl moiety of the compound is also converted to the hydroxybenzoyl form. This is then followed by iodination and amination to yield the subject compound. The subject compounds can also be converted to their various salt forms. In addition, the ring members can be substituted, e.g., by alkylation, acylation, or amidation reactions, and the ester function can be modified to a series of various analogs having similar therapeutic properties.

An alternative synthesis procedure, which also uses salicylaldehyde as a starting compound, involves a cyclization step to form 2-acetylbenzofuran. This compound is then converted to its thiomorpholide derivative, which can be further converted to 2-benzofurane acetic acid, which is also formed in the other described synthesis procedure. The synthesis procedures are identical after formation of 2-benzofurane acetic acid.

The subject invention thus involves the innovative development of a Class-III antiarrhythmic agent having significantly lower toxicity than any currently available compound useful in patients with congestive heart failure (CHF).

BRIEF DESCRIPTION OF THE DRAWINGS

FIG. 3A is the change in atrial rate versus time plots for equimolar concentrations of amiodarone (▽) and compound A (●), versus a control (○). FIG. 3B is the change in atrioventricular (AV) interval plots for equimolar concentrations of amiodarone (▽) and compound A (●), versus a control (○). FIG. 3C is the change in QRS interval (intraventricular conduction time) plots for equimolar concentrations of amiodarone (▽) and compound A (●), versus a control (○). FIG. 3D is the change in QT interval (repolarization time) plots for equimolar concentrations of amiodarone (▽) and compound A (●), versus a control (○).

FIG. 4A is the change in S–H interval (atrioventricular nodal conduction time) plots for equimolar concentrations of amiodarone (●) and compound A (▽), versus a control (○). FIG. 4B is the change in HV interval (His-Purkinje conduction time) plots for equimolar concentrations of amiodarone (●) and compound A (▽), versus a control (○). FIG. 4C is the change in QRS interval (intraventricular conduction time) plots for equimolar concentrations of amiodarone (●) and compound A (▽), versus a control (●). FIG. 4D is the change in QT interval (repolarization time) plots for equimolar concentrations of amiodarone (○) and compound A (▽), versus a control (○).

DETAILED DISCLOSURE OF THE INVENTION

Figure 1A:
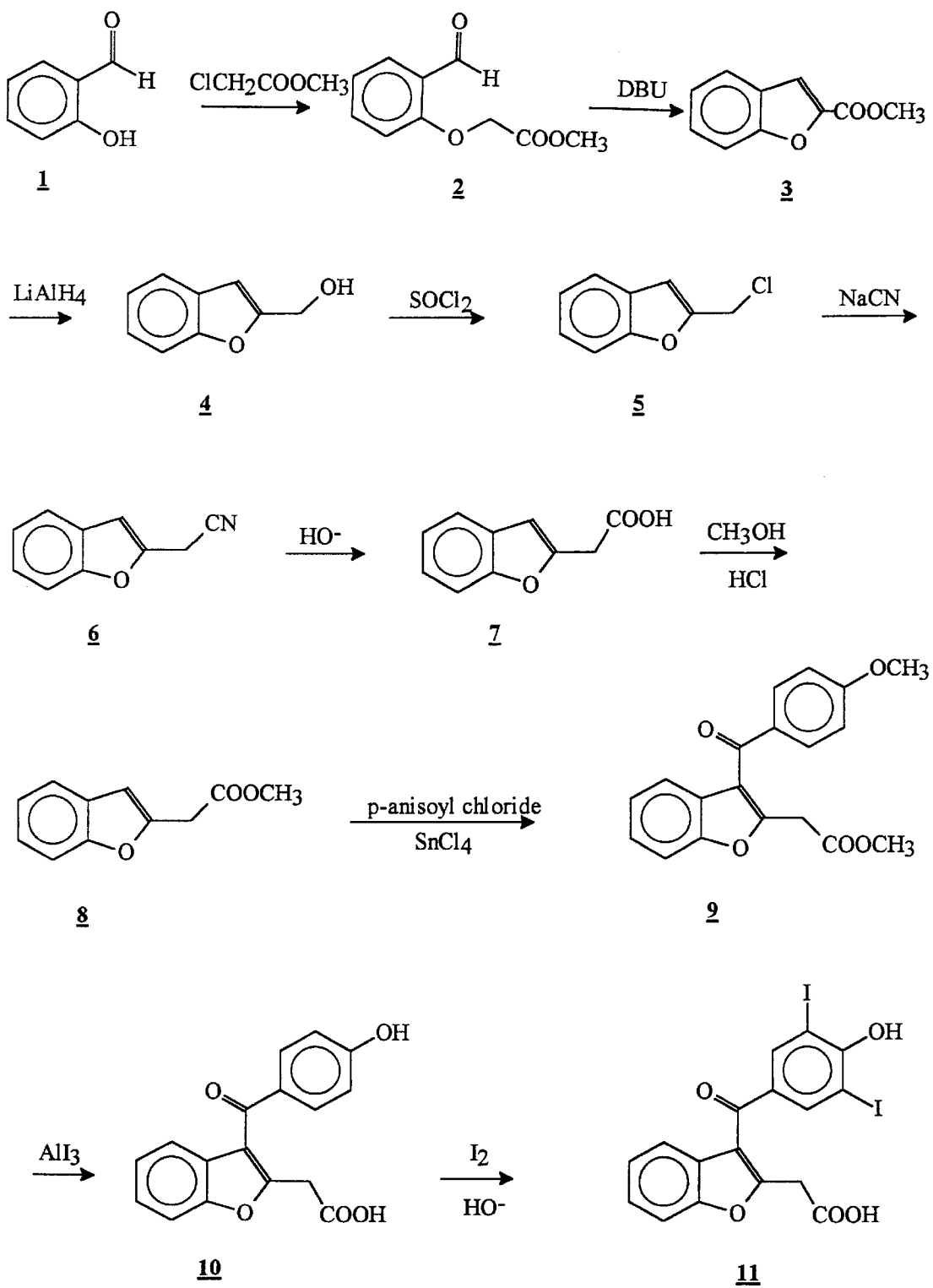
FIGS. 1a and 1b show the step-wise reaction scheme which results in the synthesis of the novel compound, methyl 2-[3-(3,5-diiodo-4-diethylamninoethoxybenzoyl) benzofurane]acetate and its hydrochloride salt form.

The subject invention concerns novel compounds which can produce the desired pharmacological properties of amiodarone but, unlike amiodarone, are susceptible to biotransformation by plasma and tissue esterases to give a carboxylic acid metabolite. Carboxylic acids can form water-soluble salts at physiological pH, and therefore can undergo renal elimination. As a consequence, the novel compounds, exemplified herein by compound A, can have shorter elimination half-life. Accordingly, long-term toxicity symptoms (pulmonary fibrosis, corneal microdeposits, etc.) decrease.

One novel compound of the subject invention has the chemical name methyl 2-[3-(3,5-diiodo-4-diethylaminoethoxybenzoyl)benzofurane] acetate and has the chemical structure shown below.

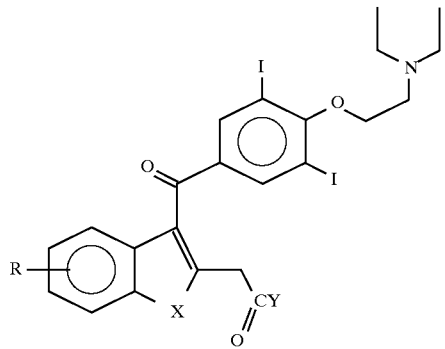

wherein R=H, OH, $NH_2$, SH, halide, alkyl, O-alkyl, acyl, O-acyl, aryl, O-aryl, substituted amine, or substituted thiol.

Y=$OR_1$, wherein $R_1$ is a straight or branched chain alkyl or heteroalkyl having 1 to 8 carbon atoms, a substituted or unsubstituted aryl or heteroaryl; or

wherein $R_2$ and $R_3$ are independently selected from H, alkyl or heteroalkyl of 1 to 6 carbon atoms, or wherein N is part of a cyclic or heterocyclic group, preferentially, but not limited to, morpholine, triazole, imidazole, pyrrolidine, piperidine, piperazine, pyrrole, dihydropyridine, aziridine, thiazolidine, thiazoline, thiadiazolidine, or thiadiazoline.

The structure, as shown, includes an iodinated benzene ring moiety. It would be understood by an ordinarily skilled artisan that other halides, including fluorine, bromine, or chlorine, can be substituted for the iodine substituents. Thus, these other halogenated compounds are contemplated to be included as part of the invention.

The novel compounds can also be provided in their salt form, preferably the hydrochloride salt. Other salts of the novel compounds would be recognized by those of ordinary skill in the art. In addition, the ring structure moieties of the novel compounds can be derivatized by methods and procedures well known by those of ordinary skill in the art. For example, it would be well known that various R-groups can be attached to the six-membered ring of the benzofuran moiety of the subject compound, wherein the R groups can include H, OH, $NH_2$, SH, halides, alkyl, O-alkyl, acyl, O-acyl, aryl, O-aryl groups, substituted amines, and substituted thiols. In a preferred embodiment, R is H and X is O.

The subject invention encompasses the novel compound A and compositions comprising these compounds. The successful application of the new compounds to the treatment of CHF is evidenced by the evaluation of the thermodynamic properties of the compound, e.g., measuring its partition coefficient between water and octanol, evaluation of its kinetics of elimination by measuring its stability in buffer and in human plasma, and evaluation of its electrophysiological properties in guinea pig heart preparations. See Examples hereinbelow. More specifically, the novel compounds can be used for treating life-threatening ventricular tachyarrhythmias, especially in patients with congestive heart failure. This product can provide effective management of not only ventricular tachyarrhythmias and less severe ventricular arrhythmias, but also atrial fibrillation and re-entrant tachyarrhythmias involving accessory pathways. A composition comprising a novel compound having a rapid elimination rate can offer many advantages over the currently available antiarrhythmic agents such as amiodarone. These advantages include:

(i) a shorter onset of action, (ii) decreased and more manageable long-term toxicity, and (iii) lower potential for drug interactions.

In addition, the novel compounds can be included in a composition comprising a second active ingredient. The second active ingredient can be useful for concurrent or synergistic treatment of arrhythmia or for the treatment of an unrelated condition which can be present with or result from arrhythmia or CHF.

The subject compounds have thermodynamic properties similar to those of amiodarone, as suggested by log P measurements, but provide the advantageous property of being rapidly metabolized in plasma to a water-soluble metabolite. More specifically, the subject compounds are Class-III agents with electronic, steric, and thermodynamic properties comparable to those of amiodarone, but with an enzymatically labile ester group advantageously built into the structure such that the drug can be readily hydrolyzed in plasma to a polar, water-soluble metabolite. This water-soluble metabolite can be eliminated by the kidneys. This is a definite advantage over amiodarone, which is metabolized primarily in the liver. Under such conditions, the elimination of the novel compound A is increased and results in a more rapid dissociation of the drug from phospholipid-binding sites. The accumulation of the compound, which is dependent on the steady-state tissue concentration of the drug, and therefore on the dose, then becomes easily reversible. It follows that, upon discontinuation of a drug comprising one of the novel compounds, clearance from the body is more rapid. This increased elimination makes antiarrhythmic therapy using the subject compounds or compositions comprising the subject compounds easier to manage.

Following are examples which illustrate procedures, including the best mode, for practicing the invention. These examples should not be construed as limiting. All percentages are by weight and all solvent mixture proportions are by volume unless otherwise noted.

EXAMPLE 1

Synthesis of the Novel Compound

Figure 1B:
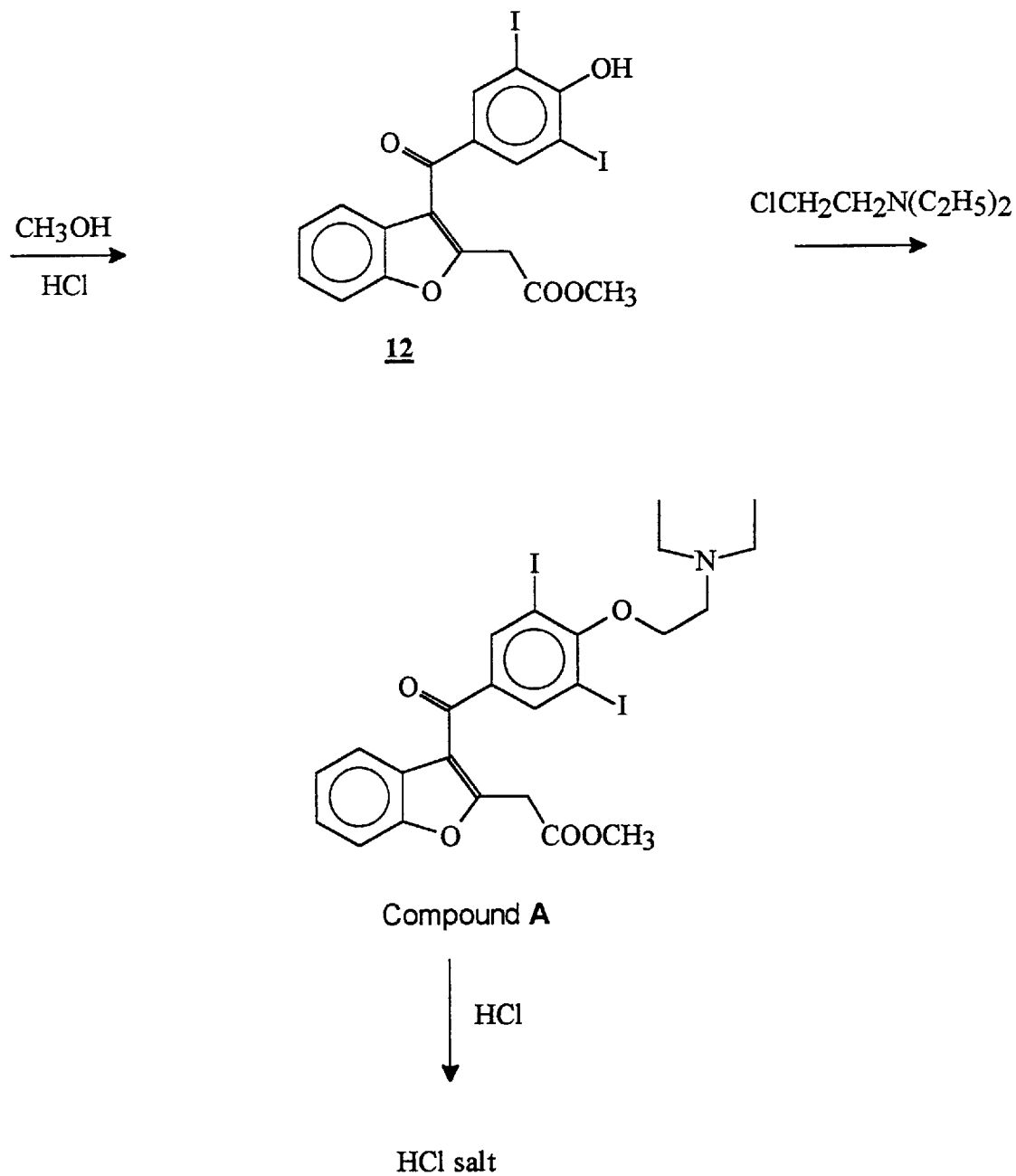

The novel compounds can be synthesized according to the scheme set out in FIGS. 1A and 1B. Below, the steps of the procedure, as shown in FIGS. 1A–1B, are described in detail. The primary compounds involved in the synthesis step are numbered corresponding to the numbers provided in FIGS. 1A and 1B.

Methyl o-formylphenoxyacetate: 2. Approximately 509 g of the starting compound, salicylaldehyde (1) was introduced into a 4-liter Erlenmeyer flask with powdered potassium carbonate (569 g), dimethylformamide (1,000 ml), and methyl chloroacetate (478 g) and mechanically stirred at 65° C. for about 24 hours. The stirring was stopped and the reaction mixture cooled to 25° C. The mixture was poured into cold water (0° C.) while stirring vigorously. An oil separated that suddenly solidified. Stirring was continued for 30 minutes and the solid isolated by filtration. The product was washed with water (2×1,000 ml) and pressed dry. The product can also be dried in vacuo at 25° C. A small sample (approx. 2 g) was purified by distillation. The boiling range of the pure product is 124°–128° C. at 2 mm Hg and has a melting temperature range of about 50.2°–50.6° C.

Methyl 2-benzofuranecarboxylate: 3. The crude product 2 was placed into a 5-liter 3-necked round-bottomed flask equipped with a mechanical stirrer and a water trap. Toluene (1,900 ml) was added and the solution heated at reflux temperature (111° C.) until all water had been removed. Diazabicyclounde-7-ene (DBU) (65 g) was then added and the mixture was stirred at 111° C., without the water trap, until the starting material was no longer present, i.e., was not detectable by TLC monitoring. Most of the solvent (90%) was then distilled off. The residue was cooled to 25° C., and ethyl acetate (1,000 ml) was added. The mixture was transferred to a separatory funnel and the organic solution washed with 2N HCl (2×1,000 ml), then with water (1,000 ml). Drying was done over magnesium sulfate. The crude product (326.56 g) was a dark oil and was used directly in the next step. A small sample was purified for the purpose of structure elucidation: the crude material (2 g) was dissolved in ethyl ether and washed with 1N KOH. Drying was done over magnesium sulfate, the material was filtered, and the solvent evaporated. The oily residue was crystallized from isopropanol. The melting range is 53.8°–54° C.

2-Hydroxymethylbenzofuran: 4. The crude product 3 (324 g) was dissolved in anhydrous ethyl ether. The solution was kept under inert atmosphere (nitrogen or argon) and cooled to 0° C. in an ice bath. A 1M solution of lithium aluminum hydride in ether (620 ml) was added dropwise, while stirring, over a period of 1 hour. The solution was then washed with 2N HCl (4×1,000 ml), with 2N KOH (2×500 ml), and with water (1,000 ml). The material was dried over magnesium sulfate, filtered, and the solvent evaporated. The crude product was distilled in vacuo, yielding approximately 155.36 g (1.05 mol). The boiling point is 110° C. at 1.5 mm Hg.

2-Chloromethylbenzofuran: 5. Compound 4 (155.25 g) was dissolved in anhydrous ethyl ether (250 ml) containing dimethylformamide (1 ml). The reaction flask was placed into an ice bath, and when the solution temperature was between 0° C. and 4° C., thionyl chloride (124.3 g, 76.2 ml) was added dropwise, while stirring, over the period of 1 hour. The mixture was then stirred for another hour, washed with water (250 ml), 3% sodium bicarbonate solution (250 ml), and with water again (250 ml). The material was dried over magnesium sulfate, filtered, and the solvent evaporated. The product was distilled in vacuo, and the yield was approximately 117 g. The boiling point is about 78° C. at 1.5 mm Hg.

2-Cyanomethylbenzofuran: 6. Compound 5 (117 g) was added dropwise to a stirring suspension of sodium cyanide (37.64 g) in dimethyl sulfoxide (100 ml). The reactor was placed from time to time into an ice bath in order to keep the reaction temperature between 20° C. and 45° C. Addition lasted 60 minutes. The reaction mixture was stirred for another 16 hours, then poured into methylene chloride (500 ml), washed with water (500 ml, then 2×250 ml), and evaporated to dryness. A small sample was purified on a silica gel column, eluting with dichloromethane/hexanes (50:50 v/v).

2-Benzofuraneacetic acid: 7. The crude cyanomethylbenzofuran, compound 6, was stirred for 6 hours in boiling water (1,000 ml) containing sodium hydroxide (80 g), cooled to 25° C., then washed with methylene chloride (250 ml, then 2×100 ml). The pH was brought to 2.0 with 6N HCl. The precipitate was extracted with methylene chloride (200 ml, then 100 ml, then 50 ml), dried over magnesium sulfate and the solvent evaporated. The yield was approximately 72 g.

Methyl 2-benzofuraneacetate: 8. Compound 7 (72 g) was dissolved in methanol (200 ml) and the solution saturated with dry HCl. The solution was refluxed for 2 hours and the solvent evaporated. The residue was dissolved in methylene chloride (200 ml) and the solution washed with 5% sodium bicarbonate, and then with water (100 ml). The residue was dried over magnesium sulfate and the solvent was evaporated. The product was distilled in vacuo. The yield was approximately 67.3 g.

Methyl 2-(3-anisoylbenzofurane)acetate: 9. Compound 8 (67 g), anhydrous 1,2-dichloroethane (250 ml), and p-anisoyl chloride (59.65 g) were added in a 1,000-ml flask under inert atmosphere. The solution was cooled in an ice bath, and $SnCl_4$ (115 ml) was added slowly. The bath was allowed to warm up to 25° C. and the solution was then stirred for another 24 hours. The solution was poured into an ice/water mixture (1,000 ml). The organic phase was collected, washed with 3% sodium bicarbonate (2×500 ml) and with water (500 ml), and then dried over magnesium sulfate. The solvent was evaporated. The oily residue was stirred for 24 hours into hexane (100 ml). The product is a pale yellow powder. The yield was approximately 103.3 g.

2-(3-p-hydroxybenzoylbenzofurane)acetic acid: 10. Aluminum powder (45 g), benzene (900 ml), and iodine crystals (345 g) were introduced in a 2-liter flask with efficient reflux condenser and mechanical stirrer. The solution was placed in a water bath and stirred until most of the heat had dissipated, then stirred at reflux temperature until the red color of iodine disappeared (approx. 30 minutes). This mixture was cooled to 25° C. then, while stirring, compound 9 (70 g) and tetrabutylammonium iodide (0.86 g) were added. When addition was complete, a portion of the solvent (600 ml) was distilled away, then the remaining solution was cooled to 25° C. A portion of ice-water (700 ml) was slowly added, followed by ethyl acetate (600 ml). The resulting suspension was filtered and the residue washed with more ethyl acetate (2×50 ml). The organic phase was washed with more water (500 ml), then extracted with 3% sodium bicarbonate (3×1, 200 ml). The combined aqueous phases were washed with ethyl acetate (200 ml). The aqueous solution was placed into an ice bath and ethyl acetate (250 ml) was added. The solution was acidified slowly using 6N HCl while stirring. The organic phase was washed with water (200 ml), dried over magnesium sulfate, filtered, and the solvent evaporated. The yield was approximately 26 g.

2-[3-(3,5-diiodo-4-hydroxybenzoyl)benzofurane]acetic acid: 11. Compound 10 (25.25 g) was dissolved in water (250 ml) containing potassium carbonate (23.85 g). Iodine (47.57 g) was added and the mixture was stirred at 25° C. for 90 minutes. Two hundred milliliters of water was added and the solution acidified with 2N HCl. The residue was filtered, then dissolved in ethyl acetate (500 ml), washed with water (500 ml), then with 5% sodium thiosulfate (2×500 ml), then with water (500 ml). The residue was dried over magnesium sulfate, and the yield was approximately 37 g.

Methyl2-[3-(3,5-diiodo-4-hydroxybenzoyl)benzofurane] acetate: 12. Compound 11 (16.4 g) was dissolved into methanol (100 ml) and concentrated sulfuric acid (1 ml). The solution was refluxed for 1 hour, then the solvent was evaporated. The residue was dissolved in ethyl acetate (500 ml) and washed with 5% sodium bicarbonate (300 ml). Extraction was done with 0.15N NaOH (3×150 ml). The solution was acidified with 6N HCl and extracted with ethyl acetate (2×150 ml). The organic phase was washed with 1% sodium bicarbonate (2×300 ml) and dried over magnesium sulfate. The yield was approximately 11.64 g.

Methyl2-[3-(3,5-diiodo-4-diethylaminoethoxybenzoyl) benzofurane]acetate: A. Compound 12 (2.88 g) was dissolved in 0.1N NaOH solution (51 ml). Methylene chloride (25 ml) is added. Benzyltriethylammonium chloride (0.114 g) and a solution of diethylaminoethyl chloride (0.96 g) in methylene chloride (25 ml) was then added. This was stirred for 2 hours at 25° C. The organic phase was washed with 0.1N NaOH (50 ml), 1N HCl (50 ml), 0.1N NaOH (50 ml), and water (50 ml) and dried over magnesium sulfate to yield the subject compound.

EXAMPLE 2

Alternative Synthetic Route for the Novel Compounds

Figure 2:
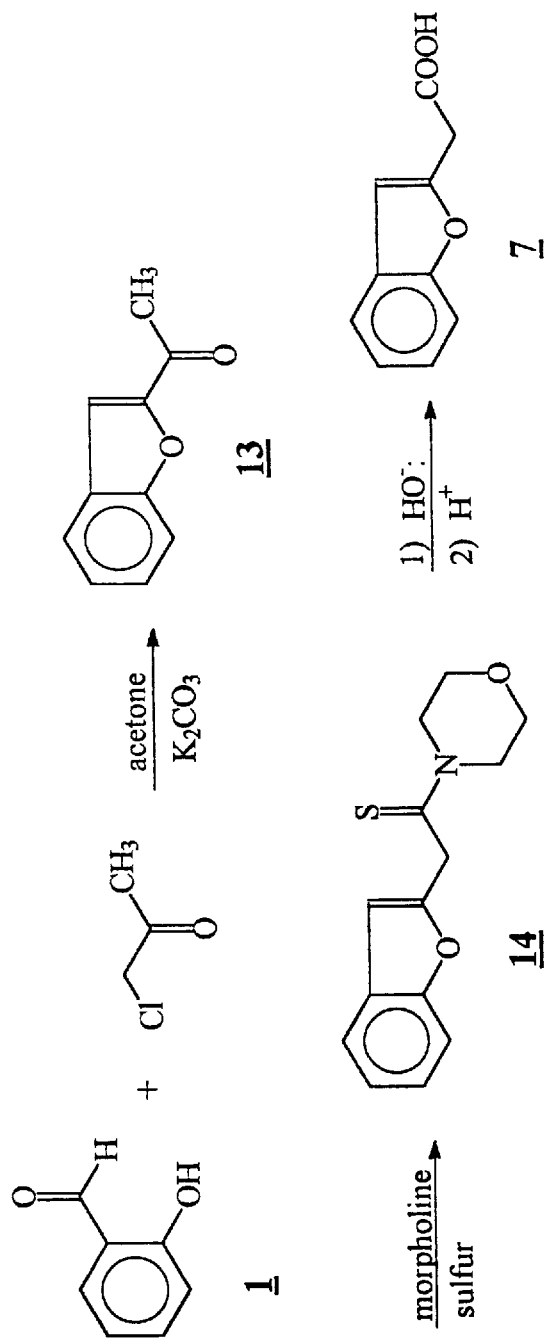
FIG. 2 shows an alternative synthetic scheme, where 2-benzofurane acetic acid, compound 7, can be made by synthesizing 2-acetylbenzofuran 13 from salicylaldehyde, followed by a chain elongation procedure known as the Willgerodt-Kindler reaction in order to make the thiomorpholide derivative 14 which is then hydrolyzed to compound 7.

An alternative synthetic scheme is shown in FIG. 2, where 2-benzofurane acetic acid, compound 7, can be made by an alternative reaction that involves synthesizing 2-acetylbenzofuran 13 from salicylaldehyde 1 reacted with chloroacetone, followed by a chain elongation procedure known as the Willgerodt-Kindler reaction in order to make the thiomorpholide derivative 14 which is then hydrolyzed to compound 7. The remainder of the synthetic scheme to the novel compound A is then essentially identical to Example 1.

1. Acetylbenzofuran 13. Salicylaldehyde (326.7 g) is introduced into a 3-liter 3-necked round-bottomed flask containing potassium carbonate (415 g) and acetone (500 ml). Chloroacetone (252.6 g) is then added dropwise, while stirring, over a period of 30 minutes, followed by addition of another portion of acetone (500 ml). The mixture is stirred at reflux temperature for 4 hours then cooled to 25° C. and filtered. The filtrate is evaporated and gives approximately 441 g of a red crystalline solid, 2-acetylbenzofuran 1, which is pure enough for step 2, below. To verify the identity of the product, a small portion was distilled in vacuo (P=0.1 mm Hg) using a short path distillation apparatus, and it was determined that the pure product distills at 80° C., yielding a white crystalline solid.

2. Benzofurane acetic acid 7. The crude 2-acetylbenzofuran 13 (441 g) is dissolved in morpholine (256.35 g) in a 3-liter 3-necked round-bottomed flask. Sulfur (≈90 g) is added, and the mixture is stirred at reflux temperature (108° C.) for 120 minutes. This reaction yields the intermediate thiomopholide derivative 14. The mixture is cooled to 25° C. Methanol (750 ml), water (500 ml), and sodium hydroxide (220 g) are added, and the mixture is stirred at reflux temperature (80° C.) for another 4 hours. A portion of the solvent (750 ml) is then removed by distillation. The volume of the solution is brought to 6 liters with water. NaOH (40 g) and activated decolorizing charcoal (5 g) are added and the mixture is stirred at reflux temperature for 60 minutes, then filtered through celite. The mixture is then acidified to pH 2 with 12N HCl, and the product is extracted with ethyl acetate. The extract is dried over sodium sulfate and evaporated, yielding approximately 289 g of a dark solid. The crude product can be used for the next step without further purification. All physical properties of this product are identical to compound 7, and can be used in an identical manner as compound 7 in the synthesis scheme described in Example 1, above.

EXAMPLE 3
Partition Coefficient of Novel Compounds

The thermodynamic properties of the new compound A can be evaluated by measuring its partition coefficient, P, between a pH 7.4 phosphate buffer and octanol. The buffer solution and octanol are mutually saturated before the experiment. The test compounds can be dissolved in the octanol:buffer mixture at such a concentration that neither phase is saturated. The volume ratio between buffer and octanol is adjusted so that the concentration of compound in water after equilibrium is measurable. The mixture is shaken for 1 hour and centrifuged in order to obtain complete separation of the two phases. The concentration of test compound can be measured in the aqueous phase before and after equilibrium, using a UV detection method. The partition coefficient can be calculated using the following equation:

$$P = C_O/C_W$$

where P is the partition coefficient, and $C_O$ and $C_W$ are the concentrations of test compounds in octanol and in water, respectively. Since measurements take place only in aqueous buffer, the equation has to be modified to the following, which can be used in this experiment:

$$P = [(Q_i - Q_W)/Q_W] \times V_W/V_O$$

where $Q_i$ is the initial amount of test compound introduced in the buffer:octanol mixture, $Q_W$ is the amount of test compound in buffer phase after equilibrium has been reached, and $V_W$ and $V_O$ are the volumes of buffer and octanol, respectively.

EXAMPLE 4
Stability in Buffer and Metabolism Rate in Human Plasma

Analytical method. Standard HPLC techniques can be used to determine the concentration of the drug in buffer and in human plasma using standard analytical procedures known in the art.

Stability in buffer. A known concentration of the novel compound A can be incubated in a pH 7.4 phosphate buffer at 37° C. Aliquots of the solution can be taken at various recorded intervals and diluted to the appropriate concentration for injection into the HPLC system. The hydrolysis rate constant, K, in buffer can be calculated from the plot of drug concentration vs. time.

Metabolism rate in human plasma. The same procedure as above can be used with human plasma instead of buffer. The rate constant in plasma can be compared to the rate constant in buffer in order to give an approximated rate of metabolism by plasma enzymes.

EXAMPLE 5
Electrophysiological Properties in Guinea Pig Heart

Antiarrhythmic activity in guinea pig heart preparations can be tested for the novel compound A by methods and techniques well known by those of ordinary skill in the art. Antiarrhythmic activity in guinea pig heart preparations is accepted in the art as a model for antiarrhythmic activity in humans. Specifically, activity in guinea pig heart preparations is used to show that a compound depresses the spontaneous discharge, slows the sinus node spontaneous firing rate, prolongs the effective refractory period (ERP), slows the intra-atrial conduction, suppresses atrial premature beats, prolongs the ventricular ERP, and decreases ventricular excitability. Microelectrode and pacing techniques can be used as are standard in the art. Assays to show such activity can be conducted in the isolated, superfused guinea pig S–A node-right atrial preparation. A full dose-response curve for compound A can be calculated in each preparation in order to demonstrate the effects of different doses on S–A node spontaneous rate, atrial action potential duration (APD) and ERP, and on ventricular APD and ERP. The $EC_{50}$ (the effective concentration that produces 50% of the maximum response), as well as the threshold and maximum doses for the compound can be determined from the full dose-response curve.

The results of electrophysiological studies carried out in guinea pig isolated hearts using the subject compound, compound A, showed that compound A displays electrophysiological properties classically associated with Class III antiarrhythmic agents. The results of these studies are shown in FIGS. 3–5. Compared to the known compound, amiodarone, the electrophysical effects of the subject compound show several advantages. For example, on an equimolar basis, the electrophysiological effects of compound A on atrioventricular conduction, intraventricular conduction and ventricular repolarization times are much greater than those of amiodarone, both in the spontaneously beating heart (see FIGS. 3A, 3C, and 3D), and in the paced heart (see FIGS. 4A, 4C, and 4D). In addition, the effects of compound A on atrioventricular conduction, intraventricular conduction and ventricular repolarization times can be partially reversed upon discontinuation of the drug, whereas the effects of amiodarone are not reversed and actually tend to continue to increase even after discontinuation of the drug. Compound A is also able to more selectively increase the time of ventricular repolarization (i.e., prolong the QT interval) relative to the changes observed on sinoatrial nodal rate and baseline atrioventricular nodal conduction time, as compared to amiodarone (FIGS. 3A–3D).

Figure 3A:
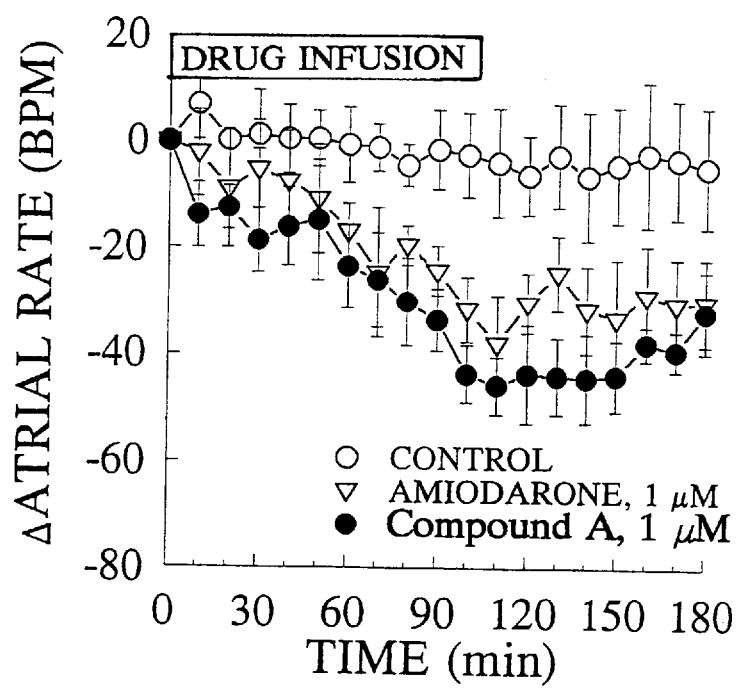
FIGS. 3A–3D show the time course of the electrophysiological effects of equimolar concentrations of compound A and amiodarone in spontaneously beating guinea pig hearts.
Figure 3B:
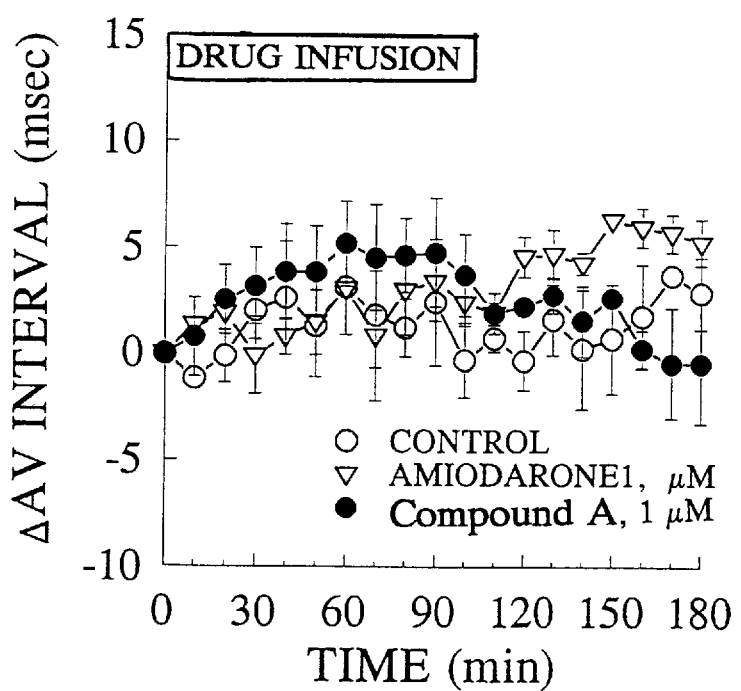
Figure 3C:
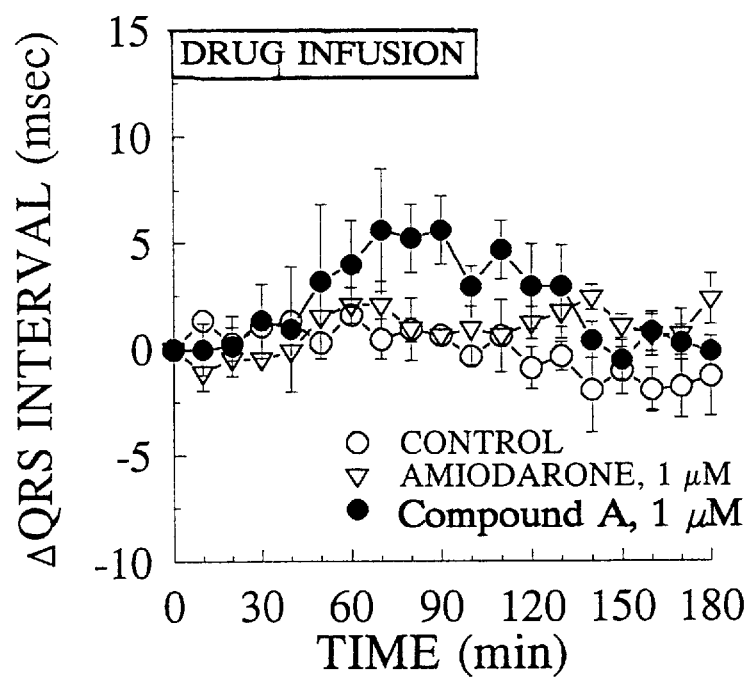
Figure 3D:
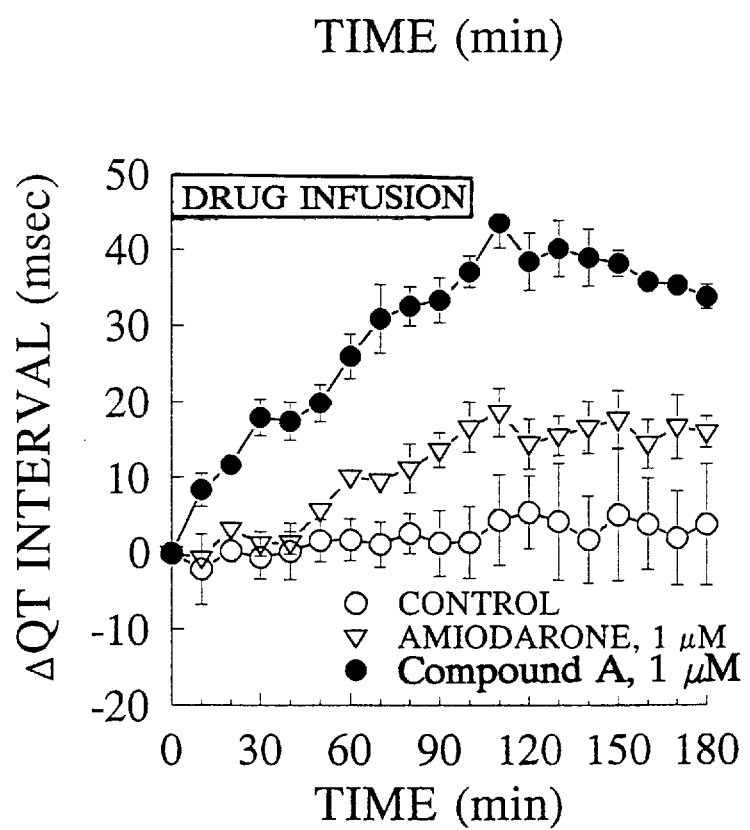
Figure 4A:
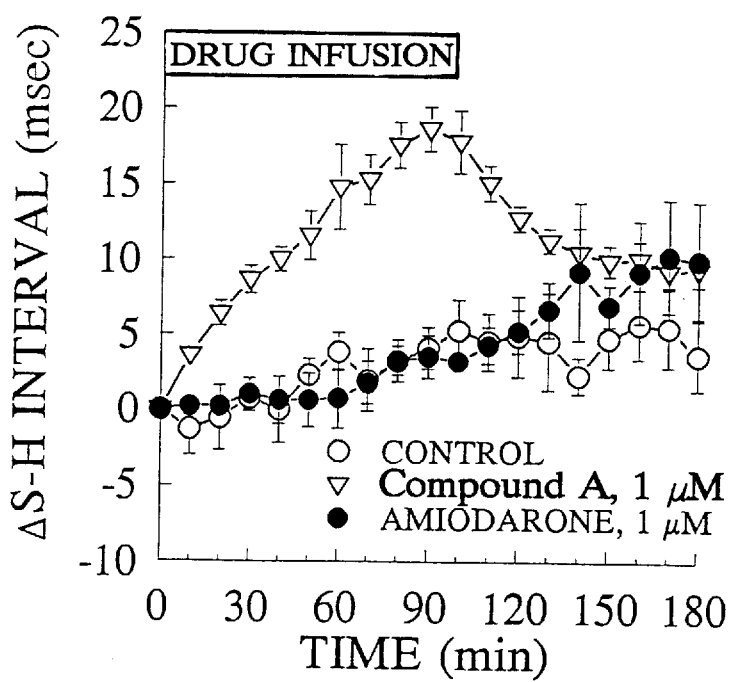
FIGS. 4A–4D show the time course of the electrophysiological effects of equimolar concentrations of compound A and amiodarone in atrially-paced guinea pig hearts.

Specifically, FIGS. 3A–3D show the time-dependent electrophysiological effects of a continuous 90-minute infusion of compound A (1 μM, n=3), amiodarone (1 μM, n=3) and vehicle (control, n=3) on the spontaneously beating heart. Changes from baseline values of atrial rate (FIG. 3A), A–V interval (FIG. 3B), QRS interval (FIG. 3C) and QT interval (FIG. 3D), respectively, are plotted as a function of time. FIG. 3A shows that, compared to control hearts, compound A and amiodarone caused significant time-dependent reductions in atrial rate of similar magnitude. In contrast, compound A and amiodarone caused only a small prolongation of the A–V interval (FIG. 3B). The minimal effect of compound A and amiodarone on atrioventricular nodal conduction in spontaneously beating hearts can be at least partly explained by noting that atrial rate modulates the effects of drugs on atrioventricular nodal conduction. That is, concomitant slowing of atrial rate will lessen the depressant effects of drugs on atrioventricular nodal conduction. For example, in paced hearts where atrial rate is kept constant, compound A (1 μM) had a much greater effect on atrioventricular nodal conduction (FIG. 4A). Unlike the effects of amiodarone, the actions of compound A on A–V interval were reversed upon discontinuation of the drug infusion, hereafter referred to as washout (FIG. 3B). In addition, compound A but not amiodarone significantly prolonged the QRS interval, i.e., slowed intraventricular conduction (FIG. 3C). During the 90-minute washout period of compound A, this effect of compound A was completely reversed. Likewise, although compound A and amiodarone significantly increased the QT interval, the effect of compound A to prolong the time for ventricular repolarization was much greater (FIG. 3D). Whereas the effect of compound A on repolarization was partially reversed during washout, the effect of amiodarone was not attenuated during washout. The average baseline values of atrial rate, A–V interval, QRS interval and QT interval were 204.6±2.4, 55.0±4.0, 21.2±0.8 and 162.5±2.9, respectively. Data are shown as mean±SEM.

Figure 4B:
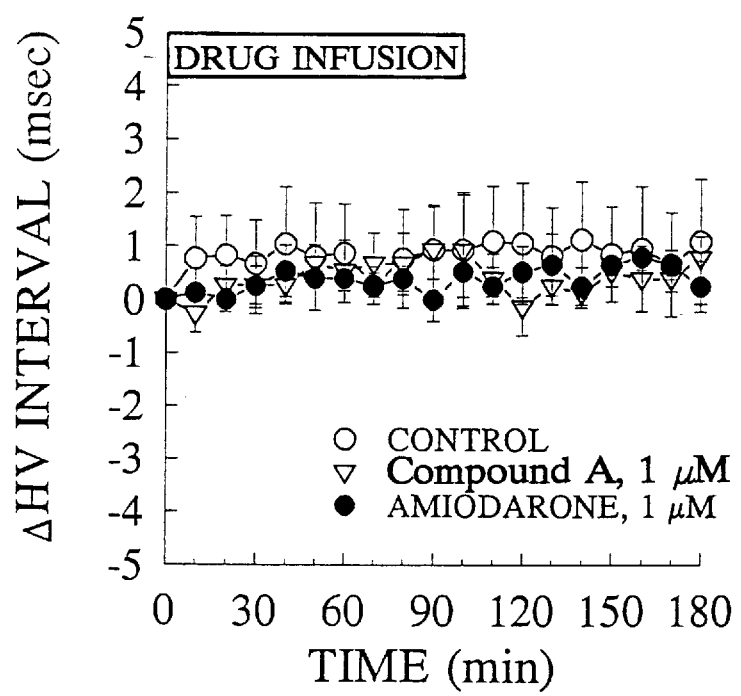
Figure 4C:
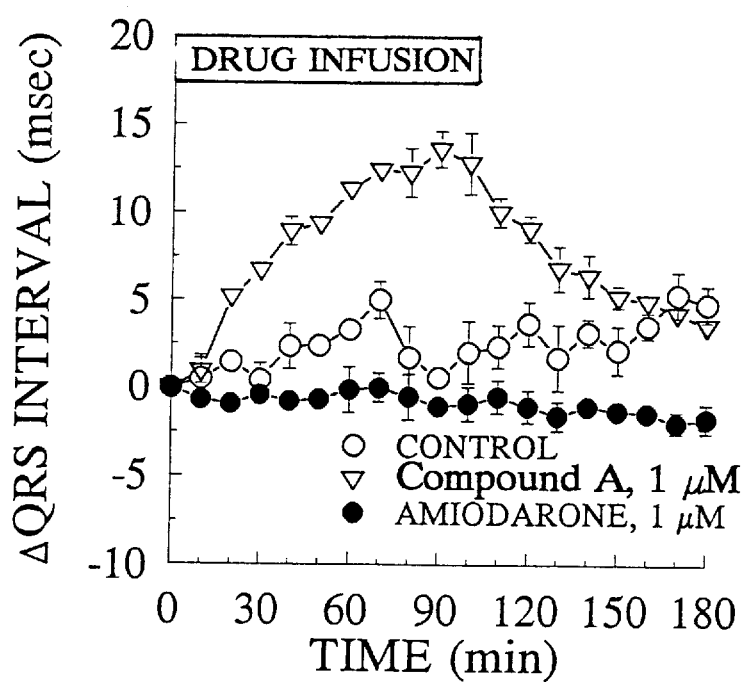
Figure 4D:
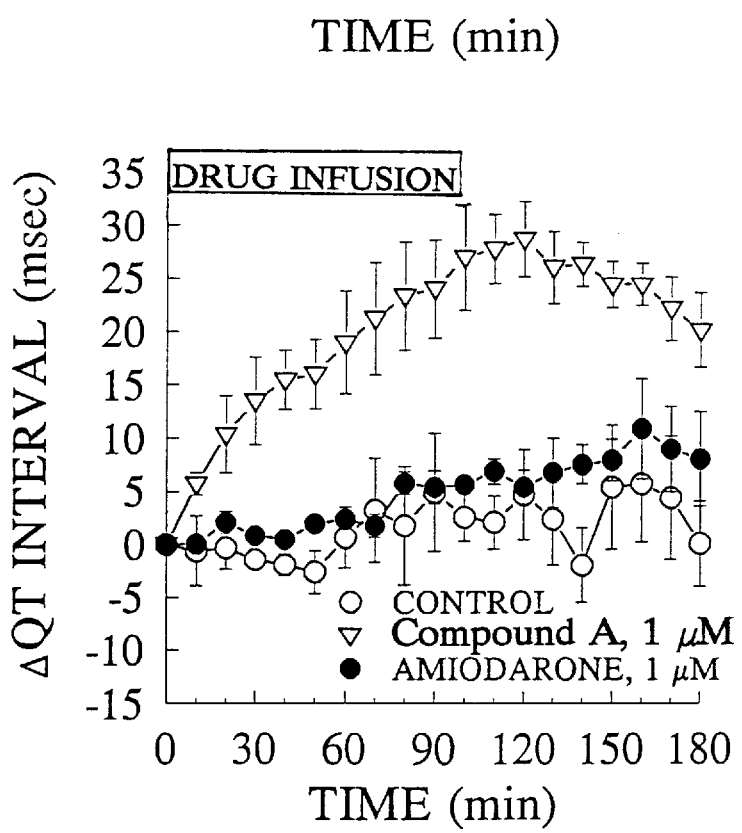
Figure 5:
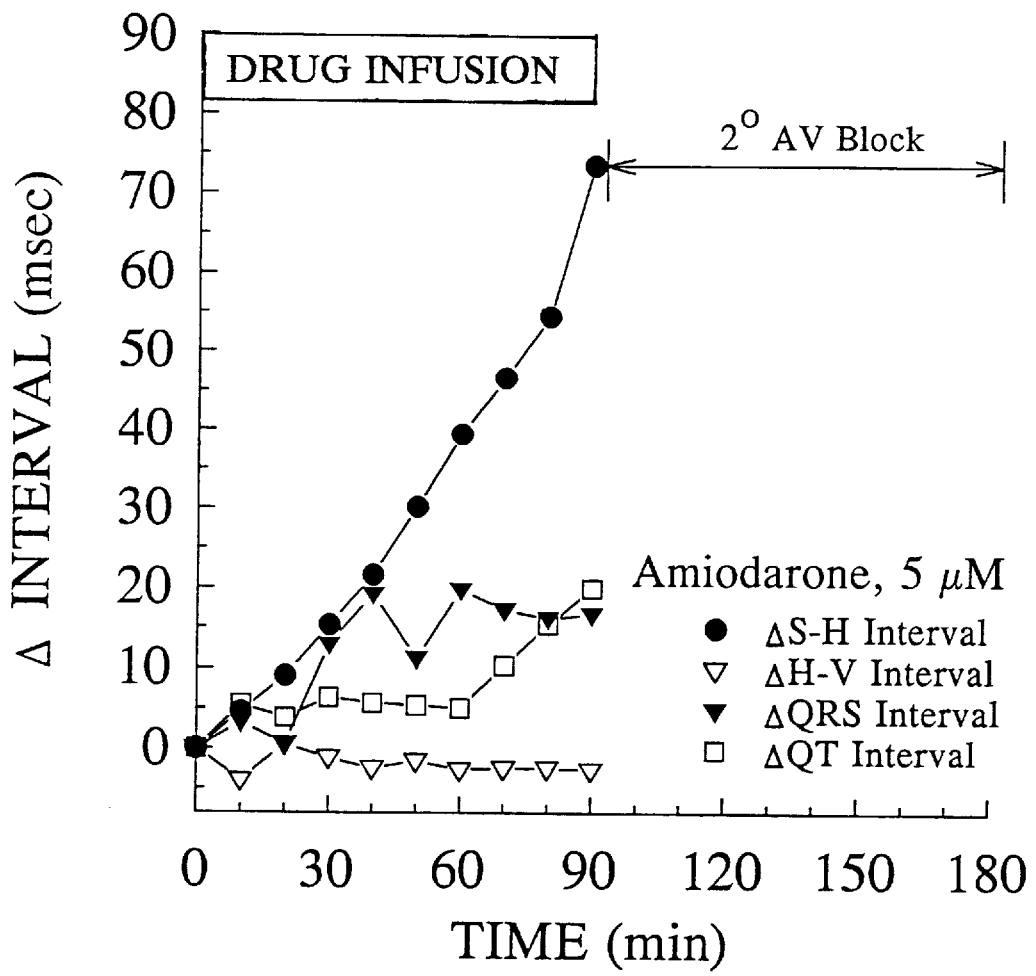
FIG. 5 shows time course of the electrophysiological effects of amiodarone (5 $\mu M$) in atrially-paced guinea pig hearts.

FIGS. 4A–4D show a series of separate experiments, the time-dependent electrophysiological effects of a continuous 90-minute infusion of compound A (1 μM, n=3), amiodarone (1 μM, n=3) and vehicle (control, n=3) in guinea pig hearts paced at 200 beats per minute was investigated. Changes from baseline values of S–H interval (FIG. 4A), HV interval (FIG. 4B), QRS interval (FIG. 4C) and QT interval (FIG. 4D), respectively, are plotted as a function of time. At equimolar concentrations, compound A depressed atrioventricular nodal conduction in paced hearts to a much greater extent than amiodarone (FIG. 4A). The prolongation of the S–H interval caused by compound A was gradual and reached a maximum of 18 msec (i.e., a 45% increase above the baseline S–H interval) before the drug infusion was stopped. Upon washout of compound A, a large fraction (≈70%) of this effect was reversed. In contrast, amiodarone had no effect on S–H interval during the period of drug infusion. Compound A and amiodarone had no effect on His-Purkinje conduction times, i.e., the HV interval remained constant (FIG. 4B). Similar to its effects on S–H interval, compound A but not amiodarone prolonged intraventricular conduction time, i.e., increased the QRS interval (FIG. 4C). The increase in QRS interval was gradual and reached a maximum of 13.5 msec (60% increase above baseline value) before the drug infusion was discontinued. The effect of compound A on intraventricular conduction was completely reversed during the 90-minute washout period. Compound A and amiodarone both significantly increased the QT interval. However, compound A was much more potent at prolonging the time for ventricular repolarization than was amiodarone (FIG. 4D). Whereas the effect of compound A on repolarization was partially reversed during washout, the effect of amiodarone was not attenuated during washout. The average baseline values of S–H interval, AV interval, QRS interval and QT interval were 40.1±1.9 msec, 7.8±0.6 msec, 22.3±0.7 msec, and 164.0±1.7 msec, respectively. Data are shown as mean±SEM.

FIG. 5 shows a comparison of the electrophysiological actions of an equipotent (to prolong the baseline S–H interval) concentration of amiodarone to those effects found using 1 μM compound A. For this purpose, a concentration of 5 μM amiodarone was selected. Whereas amiodarone (5 μM) caused a time-dependent increase in S–H, QRS and QT intervals, it had no effect on the HV interval. Of the intervals measured, amiodarone (5 μM) had the greatest effect on atrioventricular conduction time. It prolonged the baseline S–H interval by 74 msec at 90 min of drug infusion before the heart went into second degree AV block. This large prolongation of S–H interval was accompanied by only a 20 msec increase in the QT interval. On the other hand, although compound A (1 μM) caused an increase of 18 msec in the baseline S–H interval at 90-min of drug treatment (FIG. 3A), it was accompanied by an increase in the QT interval of 28 msec (FIG. 3D). Thus, compound A, compared to amiodarone, is able to more selectively prolong the time for ventricular repolarization without causing as much depression of atrioventricular nodal conduction. Likewise, as shown in FIG. 3A, at comparable degrees of atrial rate slowing, compound A was able to produce a much greater increase in the QT interval in spontaneously beating hearts (FIG. 3D). Taken together, these data show that compound A, compared to amiodarone, can prolong the ventricular repolarization time in a more selective manner at concentrations that would cause less slowing of atrial rate and atrioventricular nodal conduction. The latter is an important issue because excessive slowing of heart rate and atrioventricular nodal conduction can cause symptoms in patients.

One of the major drawbacks of amiodarone in the clinical setting is its long half-life (>30 days), which can cause severe life-threatening side effects that are slow to resolve even after discontinuation of drug therapy. The advantages of compound A over amiodarone or other currently used antiarrhythmics are that it exhibits more selective antiarrhythmic action, has a potentially shorter half-life, and has cardiac effects which are more easily reversed ("washed") upon cessation of drug treatment.

EXAMPLE 6

Uses, Formulations, and Administrations

Therapeutic and prophylactic application of the subject compounds, and compositions comprising them, can be accomplished by any suitable method and technique presently or prospectively known to those skilled in the art. Further, the compounds of the invention have use as starting materials or intermediates for the preparation of other useful compounds and compositions. The compounds of the invention are useful for various non-therapeutic and therapeutic purposes. It is apparent from the testing that the compounds of the invention have effective antiarrhythmic activity. Specifically, they are useful in regulating cardiac arrhythmia, including atrial fibrillation, in animals and humans.

The administration of the subject compounds of the invention is useful as an antiarrhythmic agent. Thus, pharmaceutical compositions containing compounds of the invention as active ingredients are useful in prophylactic or therapeutic treatment of cardiac arrhythmias in humans or other mammals.

The dosage administered will be dependent upon the immunomodulatory response desired; the type of host involved; its age, health, weight, kind of concurrent treatment, if any; frequency of treatment; therapeutic ratio and like considerations. Advantageously, dosage levels of the administered active ingredients can be, for examples, dermal, 1 to about 500 mg/kg; orally, 0.01 to 200 mg/kg; intranasal 0.01 to about 100 mg/kg; and aerosol 0.01 to about 50 mg/kg of animal body weight.

Expressed in terms of concentration, the active ingredient of the invention can be present in the new compositions for use dermally, intranasally, bronchially, intramuscularly, intravaginally, intravenously, or orally in a concentration of from about 0.01 to about 50% w/w of the composition, and especially from about 0.1 to about 30% w/w of the composition. Preferably, the novel compound is present in a composition from about 1 to about 10% and, most preferably, the novel composition comprises about 5% novel compound.

The compositions of the invention are advantageously used in a variety of forms, e.g., tablets, ointments, capsules, pills, powders, aerosols, granules, and oral solutions or suspensions and the like containing the indicated suitable quantities of the active ingredient. Such compositions are referred to herein and in the accompanying claims generically as "pharmaceutical compositions." Typically, they can be in unit dosage form, namely, in physically discrete units suitable as unitary dosages for human or animal subjects, each unit containing a predetermined quantity of active ingredient calculated to produce the desired therapeutic or prophylactic effect in association with one or more pharmaceutically acceptable other ingredients, e.g., diluent or carrier.

Where the pharmaceutical compositions are aerosols, the active ingredients can be packaged in pressurized aerosol containers with a propellant, e.g., carbon dioxide, nitrogen, propane, etc. with the usual adjuvants such as cosolvents, wetting agents, etc.

Where the pharmaceutical compositions are ointments, the active ingredient can be mixed with a diluent vehicle such as cocoa butter, viscous polyethylene glycols, hydrogenated oils, and such mixtures can be emulsified if desired.

In accordance with the invention, pharmaceutical compositions comprise, as an inactive ingredient, an effective amount of one or more non-toxic, pharmaceutically acceptable ingredient(s). Examples of such ingredients for use in the compositions include ethanol, dimethyl sulfoxide, glycerol, silica, alumina, starch, calcium carbonate, talc, flour, and equivalent non-toxic carriers and diluents.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A compound having the structure

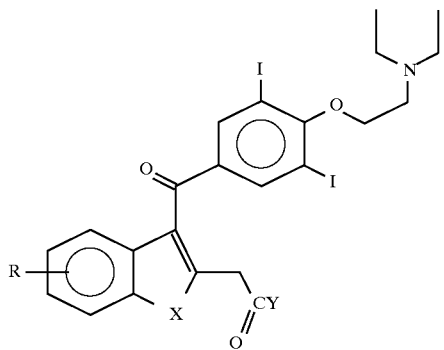

wherein R=H, OH, $NH_2$, SH, halide, alkyl, O-alkyl, acyl, O-acyl, aryl, O-aryl, substituted amine, or substituted thiol;

$Y=OR_1$, wherein $R_1$ is a straight or branched chain alkyl or heteroalkyl having 1 to 8 carbon atoms, a substituted or unsubstituted aryl or heteroaryl; or

wherein $R_2$ and $R_3$ are independently selected from H, alkyl or heteroalkyl of 1 to 6 carbon atoms, or wherein N is part of a cyclic or heterocyclic group comprising morpholine, triazole, imidazole, pyrrolidine, piperidine, piperazine, pyrrole, dihydropyridine, aziridine, thiazolidine, thiazoline, thiadiazolidine, or thiadiazoline; and X is O; a derivative of said compound; or a salt of said compound.

2. The compound, according to claim 1, wherein R is H.

3. The compound, according to claim 1, wherein the salt of said compound is selected from the group consisting of the hydrochloride, oxalate, and maleate salts.

4. The compound, according to claim 1, wherein the salt of said compound is the hydrochloride salt.

5. A pharmaceutical composition for treating cardiac arrhythmia in an animal wherein said pharmaceutical composition comprises a compound having the structure

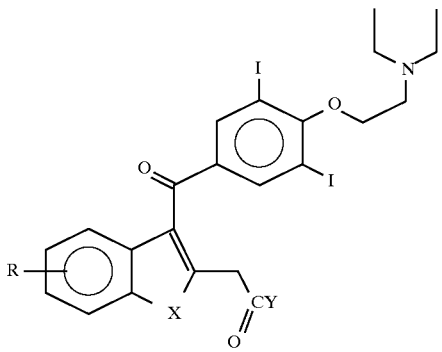

wherein R=H, OH, $NH_2$, SH, halide, alkyl, O-alkyl, acyl, O-acyl, aryl, O-aryl, substituted amine, or substituted thiol $Y=OR_1$, wherein $R_1$ is a straight or branched chain alkyl or heteroalkyl having 1 to 8 carbon atoms, a substituted or unsubstituted aryl or heteroaryl; or

wherein $R_2$ and $R_3$ are independently selected from H, alkyl or heteroalkyl of 1 to 6 carbon atoms, or wherein N is part of a cyclic or heterocyclic group comprising morpholine, triazole, imidazole, pyrrolidine, piperidine, piperazine, pyrrole, dihydropyridine, aziridine, thiazolidine, thiazoline, thiadiazolidine, or thiadiazoline;

X is O; a derivative of said compound; or a salt of said compound; and a pharmaceutically acceptable carrier.

6. The pharmaceutical composition, according to claim 5, wherein R is H.

7. The pharmaceutical composition, according to claim 5, wherein the salt of said compound is selected from the group consisting of the hydrochloride, oxalate, and maleate salts.

8. The pharmaceutical composition, according to claim 7, wherein the salt of said compound is the hydrochloride salt.

9. The pharmaceutical composition, according to claim 5, wherein said pharmaceutical composition comprises about 0.01% to about 50% of said compound.

10. The pharmaceutical composition, according to claim 5, wherein said composition comprises from about 0.1% to about 30% of said compound.

11. The pharmaceutical composition, according to claim 5, wherein said pharmaceutical composition comprises from about 1% to about 10% of said compound.

12. A method for treating cardiac arrhythmia in an animal, wherein said method comprises administering an effective amount of a compound having the structure

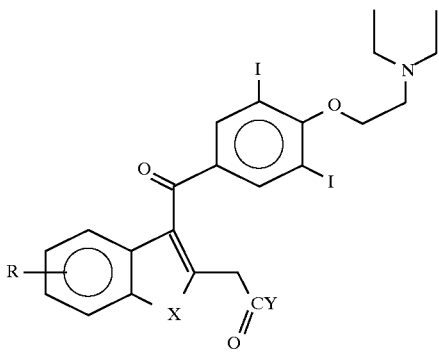

wherein R=H, OH, $NH_2$, SH, halide, alkyl, O-alkyl, acyl, O-acyl, aryl, O-aryl, substituted amine, or substituted thiol, Y=$OR_1$, wherein $R_1$ is a straight or branched chain alkyl or heteroalkyl having 1 to 8 carbon atoms, a substituted or unsubstituted aryl or heteroaryl; or

wherein $R_2$ and $R_3$ are independently selected from H, alkyl or heteroalkyl of 1 to 6 carbon atoms, or wherein N is part of a cyclic or heterocyclic group comprising morpholine, triazole, imidazole, pyrrolidine, piperidine, piperazine, pyrrole, dihydropyridine, aziridine, thiazolidine, thiazoline, thiadiazolidine, or thiadiazoline; and X is O; a derivative of said compound; or a salt of said compound.

13. The method, according to claim 12, wherein R is H.

14. The method, according to claim 12, wherein said composition is administered to a mammal.

15. The method, according to claim 14, wherein said composition is administered to a human.

16. The method, according to claim 12, wherein said composition is administered in combination with a second pharmaceutical composition.

* * * * *

UNITED STATES PATENT AND TRADEMARK OFFICE
CERTIFICATE OF CORRECTION

PATENT NO. : 5,849,788

DATED : December 15, 1998

INVENTOR(S) : Pascal Druzgala

It is certified that error appears in the above-identified patent and that said Letters Patent is hereby corrected as shown below:

Column 1, line 62: "Ill" should read --III--; and line 65: "Ill" should read --III--.

Column 8, line 55: "1, which" should read --13, which--.

Signed and Sealed this

Thirtieth Day of March, 1999

Attest:

Q. TODD DICKINSON

Attesting Officer      Acting Commissioner of Patents and Trademarks